(12) United States Patent
Wachs et al.

(10) Patent No.: US 7,193,117 B2
(45) Date of Patent: Mar. 20, 2007

(54) METHANOL OXIDATION OVER BULK METAL VANADATE CATALYSTS

(75) Inventors: Israel E Wachs, Bridgewater, NJ (US); Laura E Briand, Buenos Aires (AR)

(73) Assignee: Lehigh University, Bethlehem, PA (US)

( * ) Notice: Subject to any disclaimer, the term of this patent is extended or adjusted under 35 U.S.C. 154(b) by 0 days.

(21) Appl. No.: 10/499,447

(22) PCT Filed: Dec. 20, 2002

(86) PCT No.: PCT/US02/40747

§ 371 (c)(1),
(2), (4) Date: Oct. 25, 2004

(87) PCT Pub. No.: WO03/053556

PCT Pub. Date: Jul. 3, 2003

(65) Prior Publication Data

US 2005/0038299 A1    Feb. 17, 2005

Related U.S. Application Data

(60) Provisional application No. 60/341,284, filed on Dec. 20, 2001.

(51) Int. Cl.
 *C07C 45/38*    (2006.01)
(52) U.S. Cl. ...................... 568/472; 568/473
(58) Field of Classification Search ............... 568/472, 568/473
See application file for complete search history.

(56) References Cited

U.S. PATENT DOCUMENTS

| | | | |
|---|---|---|---|
| 5,118,868 A | 6/1992 | Sarup et al. ............... 568/474 |
| 5,907,066 A | 5/1999 | Wachs ...................... 568/472 |
| 6,028,228 A | 2/2000 | Wachs et al. | |
| 6,084,135 A | 7/2000 | Wachs et al. | |
| 6,198,005 B1 | 3/2001 | Wachs ...................... 568/472 |

OTHER PUBLICATIONS

European Search Report dated Feb. 3, 2006.
Malinski,Chemia Stosowana, vol. 24 (1980) pp. 605-613 (with informal English Translation).
Kurina, Khimiyai Khim.Tech.vol. 26(1983) pp. 1218-1220 (with English Abstract and Informal English Translation.
Suerias, Reactivity of Solids vol. 7(1989) pp. 131-141.
Wong et al.: The Oxidation of Methanol to Formaldehyde on TiO2(11)-Supported Vanadia Films.; J.Phys,Chem; 2001; vol. 105, No. 7; pp. 1366-1373.
Lampert: "Selective catalytic oxidation: a new catalytic approach to the desulfurization of natural gas and liquid petroleum gas for fuel cell reformer applications"; POWER 5888; pp. 1-8.
Kurina et al.: "Catalytic oxidation of methanol on metal orthovanadates"; (See English abstract), 1983.
"Cubic Hypovanadate Perovskite as an Oxidation Catalyst"; Journal of Catalysis; 81; 482-484; (1983).
Malinski et al.: "Catalytic Activity of Vanadates in Oxidation of Methanol"; Journal of Catalysis; 44; 101-106; (1976).
Sakakini.: "Effect of electron exchange on the catalytic behaviour of $MgV_2O_4$-$Mg_2VO_4$ systems in methanol oxidation"; Indian Journal of Chemistry; vol. 32A; Mar. 1993; pp. 210-214.
Arora et al.: "Surface Aspects of Bismuth-Metal Oxide Catalysts."; Journal of Catalysis: 159; 1-13; (1996); Article No. 0058.

*Primary Examiner*—Sikarl A. Witherspoon
(74) *Attorney, Agent, or Firm*—Banner & Witcoff, Ltd

(57) ABSTRACT

A method wherein a methanol-containing gas stream is passed in contact with a catalyst comprising a supported or unsupported bulk vanadate catalyst in the presence of an oxidizing agent for a time sufficient to convert at least a portion of the methanol to formaldehyde ($CH_2O$).

7 Claims, No Drawings

METHANOL OXIDATION OVER BULK METAL VANADATE CATALYSTS

CROSS-REFERENCE TO RELATED APPLICATIONS

This application claims the benefit under 35 U.S.C. § 119 and 119(a) of prior filed U.S. provisional application No. 60/341,284, filed Dec. 20, 2001, the entirety of which is hereby incorporated by reference, and priority of PCT application no. US02/40747, filed Dec. 20, 2002.

BACKGROUND OF THE INVENTION

1. Field of the Invention

This invention broadly relates to a catalytic composition suitable for the selective oxidation of methanol to formaldehyde. The invention is specifically directed to compositions comprising bulk metal vanadates and particularly to the use of such compositions as catalysts for selectively oxidizing methanol to formaldehyde.

2. Description of Related Art

The formation of formaldehyde involves the selective oxidation of methanol. One approach for converting methanol to formaldehyde involves oxidizing methanol over a silver catalyst. See, for example, U.S. Pat. Nos. 4,080,383; 3,994,977; 3,987,107; 4,584,412; 4,343,954 and 4,343,954. Typically, methanol oxidation to formaldehyde over a silver catalyst is carried out in an oxygen lean environment. One problem associated with silver catalyzed methanol oxidation is methanol leakage, i.e., high amounts of unconverted methanol.

An alternative process, which uses a methanol/air mixture (e.g., a reactant gas feed stream of methanol, excess air and an inert carrier gas) introduced over an iron-molybdate/molybdenum trioxide-type catalyst, also finds widespread use. See, for example, U.S. Pat. No. 3,983,073 (conversion of methanol to formaldehyde using $Fe_2(MoO_4)_3$ and $MoO_3$ having a molar ratio of Mo/Fe from 1.5 to 1.7 and a degree of crystallinity of at least 90%); U.S. Pat. No 3,978,136 (process for the conversion of methanol to formaldehyde with a $MoO_3/Fe_2O_3/TiO_2$ catalyst wherein the $MoO_3:Fe_2O_3$ weight ratio is between 1:1 to 10:1 and $TiO_2$ is present between 1 to 90 weight % of total oxides); U.S. Pat. No. 3,975,302 (a supported iron oxide and molybdenum trioxide catalyst wherein the atomic ratio of Mo/Fe is from 1.5 to 5); U.S. Pat. No. 3,846,341 (a shaped and optionally supported iron molybdate type catalyst having high mechanical strength made by reacting ammonium molybdate and ferric molybdate); U.S. Pat. No. 3,716,497 (an optionally shaped iron molybdate type catalyst made by admixing with $NH_4^+$ $A^-$); U.S. Pat. No. 4,829,042 (high mechanical strength catalyst of $Fe_2(MoO_4)_3$ and $MoO_3$ together with non-sintered $Fe_2O_3$); U.S. Pat. No. 4,024,074 (interaction product of $Fe_2(MoO_4)_3$, $MoO_3$ and bismuth oxide for catalyzing oxidation of methanol to formaldehyde); U.S. Pat. No. 4,181,629 (supported catalyst of iron oxide and molybdenum oxide on silica, alumina and the like); U.S. Pat. No. 4,421,938 (a supported catalyst of at least two oxides of Mo, Ni, Fe and the like); and U.S. Pat. No. 5,217,936 (a catalyst of a monolithic, inert carrier and oxides of molybdenum, iron and the like).

In comparison to the silver catalyzed processes, the iron-molybdate/molybdenum trioxide catalyzed processes produce higher yields of formaldehyde and would appear to be preferred approach. Iron-molybdate, $Fe_2(MoO_4)_3$, in combination with molybdenum trioxide, $MoO_3$, constitute the metal oxide phases of exemplary commercially available metal oxide catalysts suitable for oxidizing methanol to formaldehyde. Typically, such catalysts used in industrial and commercial applications contain an excess of $MoO_3$. Thus, for example, the molar ratio $MoO_3/Fe_2O_3$ may vary from 1.5/1 to 12/1 or more. Excess $MoO_3$ is provided to cover the surface iron sites with a monolayer of molybdenum species for efficiently oxidizing methanol to formaldehyde in high yields.

Thus, much of the formaldehyde produced by oxidizing methanol is prepared by reacting methanol with oxygen over this bulk $MoO_3/Fe_2(MoO_4)_3$ mixture.

Processes that use a bulk $MoO_3/Fe_2(MoO_4)_3$ catalyst are generally conducted using a tubular-type reactor having 10,000 to 20,000 tubes and the reaction is conducted at a temperature of 300–360° C. and typically obtains about an 88% yield of formaldehyde.

Processes that use a bulk $MoO_3/Fe_2(MoO_4)_3$ catalyst are not free of problems, however. Oxidizing methanol to formaldehyde using a metal molybdate/molybdenum trioxide type catalyst, e.g., $Fe_2(MoO_4)_3/MoO_3$, is a highly exothermic process. Heat released during the oxidation reaction increases the catalyst and/or the fixed bed reactor temperature producing hot spots on the catalyst surface. These hot spots reach temperatures high enough to volatilize $Mo/MoO_x$ species present within metal molybdate/molybdenum trioxide type catalysts. Additionally, in the presence of the methanol reactant, a volatile compound is generated between molybdenum and methanol ($Mo-OCH_3$). Thus, $Mo/MoO_x$ is sublimed, or a volatile molybdate compound is generated, as a consequence of such hot spots, and contributes to several adverse consequences.

The $Mo/MoO_3$ species migrate downstream (e.g., within an exemplary fixed bed reactor housing the catalyst) towards cooler regions of the fixed bed reactor or the like. Typically, the downstream migration of $Mo/MoO_3$ species is facilitated by the incoming flow of the reactant gas feed stream. The migrated $Mo/MoO_3$ species crystallize in the cooler downstream regions of the fixed bed reactor, for example, in the form of $MoO_3$ crystalline needles. Over time, the needle formation accumulates and ultimately obstructs the flow of the reactant gas feed stream through the fixed bed reactor. Thus, build up of $MoO_3$ crystals/needles in the downstream region causes a substantial pressure drop in the reactant gas feed stream flow rate as the reactant gas feed stream is directed downstream. This pressure drop impedes the efficient oxidation of methanol to formaldehyde. See, for example, U.S. Pat. No. 3,983,073 (col. 1, lines 35–52); and U.S. Pat. No. 4,024,074 (col. 1, lines 60–68); and U.K. Patent No. 1,463,174 (page 1, col. 2, lines 49–59) describing the aforementioned volatility problem.

Often, the $MoO_3$ needle formation that occurs in the downstream region of the fixed bed reactor is so excessive that the reactor must be shut down, the needles cleaned out, and fresh catalyst charged therein. These steps unnecessarily increase the time, cost, inefficiency and/or complexity of operating a fixed bed reactor or the like for oxidizing methanol to formaldehyde.

Even before such severe problems occur, the loss of the $Mo/MoO_3$ species from one location and their migration to another location creates regions where surface iron sites are exposed thus diminishing the catalytic activity and selectivity of the catalyst towards formaldehyde. This not only reduces the yield of the desired formaldehyde, but also increases the production of environmental hazardous gases such us $CO_x$.

While pending U.S. application Ser. No. 09/950,832 provides one approach for ameliorating this problem, there remains a need to provide alternative catalysts suitable for selectively oxidizing methanol to formaldehyde.

BRIEF DESCRIPTION OF THE INVENTION

The present invention is directed to a process for selectively oxidizing methanol to formaldehyde using compositions comprising bulk metal vanadates. According to the invention, a reactant gas stream containing methanol is passed in contact with a catalyst comprising a supported or unsupported bulk metal vanadate catalyst in the presence of an oxidizing agent; typically oxygen. The gas stream is contacted with the catalyst, in the presence of the oxidizing agent, for a time sufficient to convert at least a portion of the methanol to formaldehyde.

The bulk metal vanadate catalyst compositions useful for practicing the present invention are known in the prior art.

DETAILED DESCRIPTION OF THE INVENTION

In accordance with the present invention, a methanol-containing gas stream is contacted, under an oxidizing condition, with a bulk metal vanadate catalyst composition. The catalyst can either be unsupported, or supported on a substrate. The oxidizing conditions are selected to facilitate partial oxidation of the methanol in the stream to formaldehyde.

The gas stream containing methanol contacts the bulk metal vanadate catalyst under oxidizing conditions at a temperature in the range of 200° to 700° C., preferably in the range of 250° to 600° C. and most often in the range of 275° to 450° C. The oxidizing agent can usually be oxygen or air. The contacting of the methanol-containing gas with the bulk metal vanadate catalyst under an oxidizing atmosphere, e.g., in the presence of oxygen, and at an appropriate temperature, causes a selective conversion of the methanol to formaldehyde. The gaseous feed stream generally will comprise at least about 0.1 mole %, and preferably at least 1.0 mole % and higher of methanol, although higher concentrations may be employed. The gas stream may also include water. The gas stream preferably contacts the catalyst at a temperature of about 275° to 450° C.

To achieve high selectivity in the conversion of methanol to formaldehyde, it is important to maintain the flow rate of the gas stream to provide an amount of methanol per unit mass of catalyst in the range of $10^{-2}$ to $10^5$ cubic centimeters of methanol (assessed under standard conditions of temperature and pressure (STP)) per gram of active catalyst per minute (excluding inert ceramic components or other inert catalyst support material). Generally, higher reaction temperatures permit higher flow rates. Usually, the process can be operated at 0.1 to $10^4$, cubic centimeters (STP) of methanol per gram of catalyst per minute.

As used herein, the term "selectively" is intended to embrace the conversion of at least 1% of the methanol, preferably at least 10% of the methanol, more usually at least 50% of the methanol and most often at least 70%, and most preferably 95% of the methanol, which contacts the catalyst, to formaldehyde. Selectivity (expressed as a percentage), as that term is used herein, is determined by dividing the moles of formaldehyde in the methanol conversion products by the moles of methanol converted (consumed) from the feed to the reactor times 100. Selectivity indicates the percentage of formaldehyde formed as compared to the percentage of non-formaldehyde oxidation products of methanol such as CO, $CO_2$, dimethoxymethane (DMM), dimethyl ether (DME), etc. As used herein, the term conversion is determined by dividing the difference between the number of moles of methanol fed to the fixed bed reactor in the reactant gas feed stream minus the number of moles of methanol exiting the reactor by the total number of moles of methanol fed times 100. As with selectivity, conversion also is a percentage value. Conversion indicates the percentage of the moles of methanol that were oxidized to formaldehyde and any other non-formaldehyde oxidation products of methanol. Thus, if 2 moles of methanol are fed into the fixed bed reactor (e.g., in a reactant gas feed stream) yielding 1 mole of formaldehyde and 1 mole of methanol, then selectivity would equal 100% while conversion would equal 50%. Likewise, if 3 moles of methanol are fed into the fixed bed reactor (e.g., in a reactant gas feed stream) yielding 2 moles of formaldehyde and 1 mole of methanol, then selectivity would equal 100% while conversion would equal 66 and ⅔%.

The oxidation reaction is exothermic. As recognized by those skilled in the art, a variety of reactor designs, such as tubular reactors, may be employed to accommodate the necessary mass and heat transfer processes for effective operation of the process on a continuous basis. The reaction may be conducted at atmospheric pressure and above, or below atmospheric pressure. Suitable exemplary reactor temperatures range from about 300° C. to about 450° C. Suitable exemplary reactor pressures range from about 7 psia (i.e., about ½ atm) to about 165 psia. Suitable exemplary reactant gas space velocity ranges from about 0.5 $sec^{-1}$ to about 3.0 $sec^{-1}$. Other conditions suitable for oxidizing methanol to formaldehyde are used which are well known to those of ordinary skill in the art.

The partially oxidized reactant feed gas stream is hereafter referred to as the product gas stream. Formaldehyde (FA) is a significant component of the product gas stream together with quantities of one or more of some unreacted methanol (if any), water vapor or condensed water in aerosol form or the like, an inert carrier gas (if any), oxygen, and other products such as DMM (dimethoxy methane), DME (dimethyl ether), methyl formate (MF), CO, $CO_2$ and the like.

Formaldehyde is the intended product and it can be recovered from the gaseous reaction products using any one of a number of ways known to those skilled in the art.

As will be recognized by those skilled in the art, the gases leaving the reactor may contain unreacted methanol, and will contain inert gases that may have been added, as well as formaldehyde and water. The principal by-product that is formed during the partial oxidation of methanol is carbon monoxide, which may be accompanied by a small amount of carbon dioxide.

The reaction mixture leaving the catalytic reactor is generally subject to further processing in a conventional manner. For example, the formaldehyde product can be separated in a washer (absorber), or by indirect cooling, or also by fractional cooling. For example, the washing can be performed with water, in which case a multi-stage washer can be used. An aqueous formaldehyde solution is obtained in this manner. From this solution commercial formaldehyde solutions can be prepared by distillation for immediate technical use. The formaldehyde also can be condensed out of the reaction gas together with the water that has formed. In this manner, concentrated formaldehyde solutions in common commercial form eventually can be obtained.

Other ways for isolating and recovering the formaldehyde product will be apparent to those skilled in this art and the present invention is not limited to any particular isolation and recovery technology.

Suitable bulk metal vanadate catalysts for use in connection with the present invention are known. Suitable metal vanadate catalysts will, in addition to vanadium, contain a wide variety of other metal species such as alkali metals (such as sodium (Na), lithium (Li), potassium (K) and cesium (Cs)), alkaline earth metals (such as calcium (Ca), barium (Ba), and magnesium (Mg)) and transition metals (such as copper (Cu), nickel (Ni), cobalt (Co), aluminum (Al), lead (Pb), bismuth (Bi), iron (Fe), zinc (Zn), cadmium (Cd), tellurium (Te), manganese (Mn)). Suitable bulk metal vanadate catalysts for use in connection with the present invention thus include, as non-limiting examples: $PbV_2O_6$, $Pb_2V_2O_7$, $NaVO_3$, $Na_3VO_4$, $Na_2V_6O_{17}$, $BiVO_4$, $Bi_4V_2O_{11}$ and other Bi—V—O family members, $AlVO_4$, $FeVO_4$, $Mn_3(VO_4)_2$, $Mg_2(VO_4)_2$, $Mg_2V_2O_7$, $MgV_6O_{17}$, $MgV_2O_6$, $CeVO_4$, $Zn_3(VO_4)_2$, $Zn_2V_2O_7$, $CdV_2O_7$, $VOPO_4$, $(VO)_2P_2O_7$ and other V—P—O family members, $KVO_3$, $K_2V_6O_{17}$, $(NH_4)_2V_6O_{17}$, $NH_4VO_3$, $BaV_6O_{17}$, $Tl_3VO_4$, $TlVO_3$, $TlV_3O_8$, $Tl_3V_5O_{14}$, $Tl_4V_2O_7$, $Ti_{1-x}V_xO_2$, $TiVO_4$, $TiV_2O_6$, $TiV_4O_{10}$, $NbVO_5$, $Nb_2V_2O_9$, $Nb_9VO_{25}$, $CrVO_4$, $Ni_3(VO_4)_2$, $Co_3(VO_4)_2$, $Co_3V_2O_8$, $AgVO_3$, $Cu_3(VO_4)_2$, $Cu_2V_2O_7$, $Cu_3V_2O_8$, $CuVO_3$, $CuV_2O_6$, $SbVO_4$, $VSbO_4$, $Sn_{1-x}V_xO_2$, $SrVO_4$, $Sr_2V_2O_7$, $CsVO_3$, $RbVO_3$, $ZrV_2O_7$, $V_3Zr_2O$, $NdVO_4$, $SmVO_4$, $EuVO_4$, $YVO_4$, $LaVO_4$, $ReVO_4$, $LiVO_3$, $LiV_3O_8$, $Ca(VO_3)_2$, $CaV_6O_{17}$, $Ca_6V_{10}O_{28}$, $Ca_2V_2O_7$, $Hg(VO_3)_2$, $VOSO_4$ and mixtures thereof.

Additionally, bulk and supported isopoly and heteropolyoxometalates are considered as suitable materials for methanol selective oxidation to formaldehyde. The structures considered are Keggin $XM_{12}O_{40}^{4-}$, Wells-Dawson $[(X^{n+})_2 M^{18}O_{62}]^{(16-2n)-}$ and Anderson $XO_6M_6O_{18}^{n-}$ type anions where $X^{n+}$ represents a central atom [phosphorous (V), arsenic (V), sulfur (VI), fluorine, aluminum (III), silicon (IV), iron (II), cobalt (II), copper (II), zinc (II), manganese (II), tellurium (VI), gallium (III), nickel (II), chromium (III), cobalt (II) and others] surrounded by a cage of M addenda atoms, such as tungsten (VI), molybdenum (VI), vanadium (V) or a mixture of elements, each of them composing $MO_x$ (M-oxygen) units. The addenda atoms are partially substituted by other elements, such as vanadium, transition metals, lanthanides, halogens and others. The heteropoly-anions are associated with inorganic (protons, alkaline elements and others) or organic countercations generating heteropoly acids and salts.

Methods for making bulk vanadates used in the present invention also are known to those skilled in the art. In particular, the active catalyst can be prepared by physically blending and grinding metal oxides, by coprecipitation from aqueous and non-aqueous solutions containing soluble compounds of the catalyst components in the desired molar ratio, by thermal transformation, by sol-gel formation or by any other technique that provides an intimate mixture of the vanadate constituents. For example, an aqueous solution of a water-soluble vanadium compound (e.g., ammonium metavanadate) is mixed with a water-soluble metal compound (e.g., ferric nitrate) and the solution is modified (e.g., by pH adjustment such as acidification) to cause coprecipitation of both vanadium and iron, using procedures well known to those skilled in the art. The coprecipitate can be washed to eliminate soluble salts formed during the coprecipitation reactions, filtered, dried, and then is calcined to convert the metal constituents to their active metal vanadate (oxide) form. Those skilled in the art recognize a variety of water soluble metal compounds that can be used to prepare the active catalyst. Alternatively, oxides of the respective metals may be ground together and calcined. Additional details on bulk vanadates and bulk vanadate catalysis can be found in Arora et al., *Journal of Catalysis*, 159, (1996) 1–13 (bismuth vanadates) and Wachs, I. E., Ed., Characterization of Catalytic Materials, Chapter 3 "Bulk Metal Oxides," pp. 47–68 (1992 ), which are incorporated herein by reference.

Bulk vanadate catalysts are crystalline in nature, possess long range order, and give rise to an x-ray diffraction (XRD) pattern. The crystalline form can also usually be detected with Raman spectroscopy (often more sensitive than XRD). Further, information concerning bulk metal oxide catalysts in general may be found in J. Raman Spectroscopy, 21, 683–691 (1990); J. Physical Chemistry, 95(13), 5031–5041 (1991); Solid State Ionics, 45, 201–213 (1991); J. Raman Spectroscopy, 26, 397–405 (1995); and J. Chem., Soc., Faraday Trans., 92(11), 1969–1973 (1996), and *Characterization of Catalytic Materials*, edited by Israel E. Wachs, Chapter 3, pp. 47–68 (Butterworth-Heinemann, 1992) all of which are incorporated herein by reference.

In preparing a suitable bulk vanadate catalyst, a period of thermal treatment is generally necessary to convert catalyst precursor species to active bulk catalyst. Such treatment can occur either during calcination or under reaction conditions, or using some combination thereof. Under these conditions the catalyst precursor components are transformed into the active bulk catalyst. Suitable catalyst species appear to be formed as a result of calcination at about 350° to about 850° C., preferably about 35020 to about 700° C. and most preferably about 400° to about 600° C., for a period of at least about 0.5 hour, preferably for a period of about 2 to about 3 hours. The time period may depend on equipment used, as known to those skilled in the art.

As noted above, in the broad practice of the present invention, the bulk vanadate catalyst can be either unsupported or supported. Methods for dispersing the active catalyst on a suitable support material are known. The support material usually comprises a porous refractory oxide or heteropolyoxometalate. Preferred are refractory oxides and other similar materials having a specific surface area of at least about 1 m$^2$/g. Most supports will have a specific surface area in the range of 1–20 m$^2$/g. Suitable support materials include such refractory oxides as zirconia, silica-alumina, magnesium oxide, alumina-silica-magnesia, silica-zirconia, alumina, silica, titania (titanium dioxide), silica-titania, silica-magnesia, silica-zirconia-titania and other combinations of such materials. Also available as supports are amorphous and crystalline alumino-silicates, both natural and synthetic, and crystalline silicas. Most often, the support used in the invention will be relatively inert (does not adversely affect the catalyzed reactions) with respect to the catalytic composition dispersed thereon. Oxides supported on high surface area materials such as silica, alumina or refractory monoliths are commercially available. Silica often may be the best support for the bulk vanadate.

The unsupported or supported catalyst, in turn, can advantageously be provided as a coating on a foamed ceramic, honeycomb or a monolithic carrier, such as those having a unitary cylindrical body with a plurality of fine, substantially parallel gas flow passages extending therethrough and connecting both end-faces of the carrier to provide a "flow-through" type of carrier. Such carriers may be prepared with known ceramic-like materials such as cordierite, silicon nitride, mullite, spodumene, sillimanite, petalite, and silica-carbide. Typical monolithic carriers are thin-walled channels which can be of any suitable cross-sectional shape and size such as trapezoidal, rectangular, square, sinusoidal, hexagonal, oval and circular. Such structures may contain from about 60 to 600 or more gas inlet openings ("cells") per square inch of cross section. The active supported or unsupported catalyst may also be provided as a layer on refractory particles such as spheres, ceramic rings, pellets or short, extruded segments of a refractory material such as alumina.

A supported bulk vanadate can be prepared in a variety of ways as recognized by those skilled in the catalyst art. For example, an aqueous slurry of a particulate bulk vanadate (or a precursor thereof) can be applied to the support, dried and heated (calcined) to form (adhere) a catalytic material coating. The coating slurry can be prepared by mixing the vanadate particles or precursor particles with water and ball-milling (pulverizing) the mixture to a desired particle size. The coating of catalytic material may be applied by dipping the support into the aqueous slurry of the catalyst or catalyst precursor particles. Alternatively, the catalyst precursor species, as a solution, can be incorporated onto the support by known impregnation and co-precipitation techniques, wherein the desired catalyst species are formed in part by co-precipitation directly onto the suitable support.

Preparation of active bulk vanadate catalyst in the form of pills, pellets, granules, rings, spheres and the like by comulling techniques also is known. Particulate bulk metal oxide or metal oxide precursor species optionally may be combined with an inorganic clay binder, optionally a support material and the necessary amount of water to form a paste or dough which is extruded or pelletized, dried and heat treated (calcined) to yield active catalyst of a desired extrudate form and strength. As understood by those skilled in the art, the physical properties of the extruded materials (density, macroporosity and surface area) depend on a variety of parameters.

It often is desired that the bulk vanadate used in accordance with the present invention have a surface area in the range of about 0.1 to about 150 $m^2/g$ and higher. Use of free bulk vanadate particulates might be desirable when large catalyst volumes are needed or if the catalyst bed is operated in a fluidized state. A monolithic form or deposition of the active bulk catalyst on a catalyst support, such as on an inert ceramic support, might be preferred in applications where catalyst movement is to be avoided because of concerns about catalyst attrition and dusting, and a possible increase in pressure drop across a particulate bed. In a preferred approach, a bulk vanadate supported catalyst, may use a ceramic or refractory inorganic carrier such as silicon carbide, silicon nitride, carborundum, steatite, alumina and the like, provided in the shape of rings or pellets. Typically, the active catalyst will be applied to a support, including an inert ceramic support in an amount to provide 1 to 20% by weight, and preferably 5 to 15%, of the supported catalyst.

As noted, the oxidizing agent used in the selective oxidation can usually be oxygen or air. The contacting of methanol with the bulk vanadate catalyst under an oxidizing atmosphere, e.g., in the presence of oxygen, and at an appropriate temperature, causes a selective oxidation of the methanol to formaldehyde.

EXAMPLES

To facilitate a more complete understanding of the invention, a number of examples showing catalyst preparation and use are provided below. The scope of the invention, however, is not limited to specific embodiments disclosed in these examples, which are for purposes of illustration only. In the examples the various metal salts were obtained either from Alfa Aesar or J. T. Baker at a purity of 99.9%.

Catalyst Preparation and Characterization—Bulk vanadate catalysts can be prepared as follows:

Preparation Example 1

Magnesium Vanadate ($Mg_2(VO_4)_2$)

A bulk magnesium vanadate catalyst composition was prepared in accordance with the following procedure. 5 g of hydrated magnesium nitrate ($Mg_3(NO_3)_2.6H_2O$) were dissolved in 200 ml of distilled water to which citric acid was added and the mixture was stirred to dissolve the nitrate. Citric acid was added in a quantity sufficient to ensure that the molar number of equivalent anions equaled that of cations (typically, 5–8 g.). An amount of ammonium meta-vanadate (Alpha Aesar Products 99.9%) to satisfy stoichiometry with respect to the magnesium salt was separately dissolved in 200 ml of distilled water and the solution was added to the magnesium nitrate-citric acid solution. The mixture was dried in a steambath until a glassy textured solid (precursor) was observed. The precursor was further dried in a vacuum oven overnight at a temperature of 70° C., ground and calcined in order to obtain crystalline material. The calcination was conducted at 600° C. for 4 hours.

The purity of the vanadate phase was determined by Raman spectroscopy. The spectra were obtained under ambient conditions with an $Ar^+$ ion laser (Spectra Physics Model 2020-50, excitation line 514.5 nm) delivering 15–40 mW of incident radiation. Powdered vanadate (aprox. 100–200 mg) was pressed into a thin wafer about 1 mm thick that was mounted onto a spinning sample holder and rotated at 2000 rpm to avoid local heating effects. Scattered radiation from the sample was directed into a Spex Triplemate spectrometer (Model 1877) coupled to a Princeton Applied Research OMA III optical multichanneled analyzer (Model 1463) equipped with an intensified photodiode array detector cooled to 243° K. The spectral resolution and reproducibility within 2 $cm^{-1}$.

The BET surface area of the vanadate was determined by $N_2$ adsorption at 77° K on a Quantasorb surface area analyzer (Quantachrome Corporation, Model OS-9). The magnesium vanadate exhibited a surface area (by BET) of about 24 $m^2/g$.

Preparation Examples 2–11

Selective Metal Vanadates

Using the procedure of Preparation Example 1 and the salts identified in Table 1, a variety of the corresponding bulk vanadates were prepared. In addition to the starting salt and the resulting vanadate composition, Table 1 also provides the calcination time and calcination temperature, as well as the result of the BET surface area determination.

TABLE 1

| Example | Catalyst | Precursor Salt | Calcination Temperature (° C.) | Calcination Time (Hr.) | $S_{BET}$ ($m^2/g$) |
|---|---|---|---|---|---|
| 1 | $Mg_3(VO_4)_2$ | $Mg(NO_3)_2.6H_2O$ | 600 | 4 | 24.2 |
| 2 | $AgVO_3$ | $AgNO_3$ | 400 | 48 | 0.8 |
| 3 | $NbVO_5$ | $Nb(HC_2O_4)_5$ | 500 | 12 | 15.6 |
| 4 | $Cu_3(VO_4)_2$ | $Cu(NO_3)_2.6H_2O$ | 500 | 4 | 3.3 |
| 5 | $CrVO_4$ | $Cr(NO_3)_3.9H_2O$ | 550 | 4 | 14.8 |
| 6 | $Mn_3(VO_4)_2$ | $MnCl_2.4H_2O$ | 550 | 4 | 3.1 |
| 7 | $AlVO_4$ | $Al(NO_3)_3.9H_2O$ | 600 | 48 | 8.4 |
| 8 | $Ni_3(VO_4)_2$ | $Ni(NO_3)_2.6H_2O$ | 550 | 4 | 15.3 |
| 9 | $Co_3(VO_4)_2$ | $Co(NO_3)_2.6H_2O$ | 500 | 5 | 8.9 |
| 10 | $FeVO_4$ | $Fe(NO_3)_3.9H_2O$ | 550 | 4 | 4.8 |
| 11 | $Zn_3(VO_4)_2$ | $Zn(NO_3)_2.6H_2O$ | 500 | 4 | 5.2 |

Examples 1–11

Determining Surface Active Sites and Sites and Methanol Oxidation

The numbers of active surface sites (Ns) of the various vanadate catalysts, prepared and characterized as described above, were quantified by methanol chemisorption. The catalyst was exposed to a mixture of 2000 ppm of methanol vapor in He at 100° C. to generate a stable monolayer of surface methoxy species. Methoxy species M—$OCH_3$ are the intermediates species in the production of partially oxygenated reaction products during methanol selective oxidation over the bulk catalyst. Therefore, the knowledge of the amount of surface methoxy species formed during methanol chemisorption is key for determining the number of surface active sites available for methanol selective oxidation. A detailed flow diagram of the equipment and the chemisorption technique has been published. See Briand, L. E., et al., Catal. Today 62 (2000) 219–229 and Briand, L. E., et al., J. Catal. 202 (2001) 268–278. The specific reaction rate (TOF) then can be calculated by determining the production rate of redox products and normalizing the rate to the number of surface sites available for adsorption. The turnover frequency TOF is the number of methanol moles converted per mol of active surface site per second.

Methanol oxidation steady state kinetics of the various vanadate catalysts, prepared and characterized as described above, also were obtained in a fixed-bed catalytic reactor under differential conditions (methanol conversion ≦10%) and also at high methanol conversion. The following operating parameters were used to maintain methanol conversion below 10% for methanol reaction over the vanadate catalyst: sample weight, ~10 mg, reaction temperature, 300° C.; flow rate, 100 $cm^3$ (NTP) $min^{-1}$ and feed gas composition methanol/oxygen/helium, 6/13/81 mol %.

The experiments conducted at a high methanol conversion were performed under the following operating conditions: sample weight, 30–200 mg, reaction temperature, 300° C.; flow rate, 100 $cm^3$ (NTP) $min^{-1}$ and feed gas composition methanol/oxygen/helium, 6/13/81 mol %.

The catalyst was tested for 24 hs. at the high methanol conversion in order to determine the stability under reaction conditions. The catalysts were stable under these reaction conditions. Methanol conversion and the amount of products (FA: formaldehyde, DMM: dimethoxy methane, MF: methyl formate) were quantified with an on-line gas chromatograph (HP 5840) equipped with TCD and FID detectors and two columns: capillary column (CP-sil 5CB) for methylal, dimethyl ether, methyl formate and methanol analysis and a packed column (Carboxene-1000) for CO, $CO_2$, $O_2$, formaldehyde and methanol analysis.

The results of the determinations of the number of surface active sites (Ns), the reaction rates, TOFs and selectivities of the various bulk metal vanadates of Preparation Examples 1–11 toward methanol selective oxidation at low conversions are shown below in Table 2. Table 3 presents the selectivity results for selected catalysts at high methanol conversions.

A particular advantage of the process of the present invention presents is that the bulk vanadate catalysts are more active than bulk metal molybdates and thus can be used at a lower temperatures of reaction than the current industrial processes using bulk molybdate catalysts while retaining similar yield (selectivity) to formaldehyde.

Another advantage of the bulk metal vanadates is that they do not decompose under reaction conditions (no excess of $V_2O_5$ is required). Therefore, the problems related to the catalyst deactivation and reactor plugging by $V_2O_5$ needles are avoided.

TABLE 2

| EXAMPLE | Catalyst | Ns [μmol/$m^2$] | Reaction rate[a] 300° C. [μmol/$m^2$sec] | $TOF^b$ 300° C. [$sec^{-1}$] | SELECTIVITY % | | | | |
|---|---|---|---|---|---|---|---|---|---|
| | | | | | FA | DMM | DME | MF | $CO_2$ |
| 1 | $Mg_3(VO_4)_2$ | 0.56 | 0.80 | 1.43 | 95.5 | — | — | 4.5 | — |
| 2 | $AgVO_3$ | 21.14 | 35.7 | 1.56 | 92.5 | — | — | — | 7.4 |
| 3 | $NbVO_5$ | 1.61 | 5.1 | 3.14 | 87.9 | — | 3.2 | — | 8.5 |
| 4 | $Cu_3(VO_4)_2$ | 0.98 | 6.1 | 6.21 | 95.0 | — | — | 5.0 | — |
| 5 | $CrVO_4$ | 0.70 | 10.2 | 14.42 | 98.7 | — | 0.7 | 0.6 | — |
| 6 | $Mn_3(VO_4)_2$ | 3.92 | 1.4 | 0.36 | 100.0 | — | — | — | — |

TABLE 2-continued

| EXAMPLE | Catalyst | Ns [μmol/m$^2$] | Reaction rate[a] 300° C. [μmol/m$^2$sec] | TOF[b] 300° C. [sec$^{-1}$] | SELECTIVITY % | | | | |
|---|---|---|---|---|---|---|---|---|---|
| | | | | | FA | DMM | DME | MF | CO$_2$ |
| 7 | AlVO$_4$ | 2.66 | 6.0 | 2.21 | 98.0 | — | 2.0 | — | — |
| 8 | Ni$_3$(VO$_4$)$_2$ | 0.42 | 1.8 | 4.28 | 97.3 | 2.7 | — | — | — |
| 9 | Co$_3$(VO$_4$)$_2$ | 2.38 | 5.1 | 2.14 | 100.0 | — | — | — | — |
| 10 | FeVO$_4$ | 1.96 | 7.9 | 4.00 | 100.0 | — | — | — | — |
| 11 | Zn$_3$(VO$_4$)$_2$ | 4.34 | 1.0 | 0.23 | 100.0 | — | — | — | — |

[a]Activity based on overall methanol conversion at 300° C.
[b]Turnover frequency based on methanol partial oxidation products (formaldehyde, dimethoxy methane and methyl formate) at 300° C.

TABLE 3

| Preparation Example | Catalyst | SELECTIVITY % | | | | | | |
|---|---|---|---|---|---|---|---|---|
| | | Methanol conversion % | FA | DMM | DME | MF | CO | CO$_2$ |
| 5 | CrVO$_4$ | 96.0 | 90.4 | — | 0.7 | — | 8.9 | — |
| 3 | NbVO$_5$ | 100.0 | 90.0 | — | 2.0 | — | 8.0 | — |
| 8 | Ni$_3$(VO$_4$)$_2$ | 96.2 | 94.0 | — | 1.0 | — | 5.0 | — |
| 7 | AlVO$_4$ | 90.5 | 94.5 | — | 2.0 | 1.0 | 2.5 | — |
| 9 | Co$_3$(VO$_4$)$_2$ | 81.0 | 96.6 | — | — | 1.4 | 2.0 | — |
| 10 | FeVO$_4$ | 94.2 | 95.4 | — | 0.8 | 0.8 | 3.0 | — |
| 2 | AgVO$_3$ | 92.9 | 89.3 | — | — | 0.6 | 1.5 | 8.6 |

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention.

We claim:

1. A process for producing formaldehyde from a methanol-containing gas stream which comprises combining said methanol-containing gas stream with oxygen, at a methanol to oxygen mole ratio of about 0.5 to establish oxidizing conditions, contacting said combination of methanol and oxygen with a bulk metal vanadate catalyst consisting essentially of a bulk metal vanadate selected from the group consisting of PbV$_2$O$_6$, Pb$_2$V$_2$O$_7$, NaVO$_3$, Na$_3$VO$_4$, Na$_2$V$_6$O$_{17}$, BiVO$_4$, Bi$_4$V$_2$O$_{11}$, AlVO$_4$, FeVO$_4$, Mn$_3$(VO$_4$)$_2$, Mg$_2$(VO$_4$)$_2$, Mg$_2$V$_2$O$_7$, MgV$_6$O$_{17}$, MgV$_2$O$_6$, CeVO$_4$, Zn$_3$(VO$_4$)$_2$, Zn$_2$V$_2$O$_7$, CdV$_2$O$_7$, VOPO$_4$, (VO)$_2$P$_2$O$_7$, KVO$_3$, K$_2$V$_6$O$_{17}$, (NH$_4$)$_2$V$_6$O$_{17}$, NH$_4$VO$_3$, BaV$_6$O$_{17}$, Tl$_3$VO$_4$, TlVO$_3$, TlV$_3$O$_8$, Tl$_3$V$_5$O$_{14}$, Tl$_4$V$_2$O$_7$, NbVO$_5$, Nb$_2$V$_2$O$_9$, Nb$_9$VO$_{25}$, CrVO$_4$, Ni$_3$(VO$_4$)$_2$, Co$_3$V$_2$, Co$_3$V$_2$O$_8$, AgVO$_3$, Ag$_3$VO$_4$, Cu$_3$(VO$_4$)$_2$, Cu$_2$V$_2$O$_7$, Cu$_3$V$_2$O$_8$, CuVO$_3$, CuV$_2$O$_6$, SbVO$_4$, VSbO$_4$, Sn$_{1-x}$V$_x$O$_2$, Ti$_{1-x}$V$_x$O$_2$, TiVO$_4$, TiV$_2$O$_6$, TiV$_4$O$_{10}$, SrVO$_4$, Sr$_2$V$_2$O$_7$, CsVO$_3$, RbVO$_3$, ZrV$_2$O$_7$, V$_3$Zr$_3$O, NdVO$_4$, SmVO$_4$, EuVO$_4$, YVO$_4$, LaVO$_4$, ReVO$_4$, LiVO$_3$, LiV$_3$O$_8$, Ca(VO$_3$)$_2$, CaV$_6$O$_{17}$, Ca$_6$V$_{10}$O$_{28}$, Ca$_2$V$_2$O$_7$, Hg(VO$_3$)$_2$, VOSO$_4$ and mixtures thereof, said bulk metal vanadate having been produced by precipitation from a solution of a soluble vanadate species and a soluble metal species to form a precipitate followed by calcination of the precipitate, and continuing said contacting for a time sufficient to convert at least a portion of the methanol to formaldehyde, wherein conversion of methanol is over 90.5 percent and selectivity of said conversion to formaldehyde is over 89%.

2. The process of claim 1 wherein the bulk metal oxide catalyst is supported on a refractory metal oxide.

3. The process of claim 1 wherein said contacting is conducted at a temperature between 200° and 700° C.

4. The process of claim 3 wherein said contacting is conducted at a temperature between 275° and 450° C.

5. The process of claim 4 wherein said methanol-containing gas stream is contacted with said catalyst such that between $10^{-2}$ and $10^5$ cubic centimeters of methanol contacts a gram of catalyst per minute.

6. The process of claim 5 wherein between 0.1 and $10^4$ cubic centimeters of methanol contact a gram of catalyst per minute.

7. The process of claim 1 wherein the methanol conversion is over 96%.

* * * * *

UNITED STATES PATENT AND TRADEMARK OFFICE
CERTIFICATE OF CORRECTION

PATENT NO. : 7,193,117 B2
APPLICATION NO. : 10/499447
DATED : March 20, 2007
INVENTOR(S) : Israel E. Wachs et al.

It is certified that error appears in the above-identified patent and that said Letters Patent is hereby corrected as shown below:

In Claim 1; Column 11; Line 53:
Please delete "$Co_3V_2$" and insert --$Co_3(VO_4)_2$--

Signed and Sealed this

Twenty-first Day of August, 2007

JON W. DUDAS
*Director of the United States Patent and Trademark Office*